(12) United States Patent
Hansen

(10) Patent No.: US 8,092,468 B2
(45) Date of Patent: Jan. 10, 2012

(54) DEPLOYMENT HANDLE FOR AN IMPLANT DEPLOYMENT DEVICE

(75) Inventor: Palle Hansen, Bjaeverskov (DK)

(73) Assignee: Cook Medical Technologies LLC, Bloomington, IN (US)

( * ) Notice: Subject to any disclaimer, the term of this patent is extended or adjusted under 35 U.S.C. 154(b) by 224 days.

(21) Appl. No.: 12/317,352

(22) Filed: Dec. 22, 2008

(65) Prior Publication Data

US 2009/0171428 A1 Jul. 2, 2009

Related U.S. Application Data

(60) Provisional application No. 61/009,139, filed on Dec. 26, 2007.

(51) Int. Cl.
*A61F 2/84* (2006.01)

(52) U.S. Cl. ........................ 606/108; 623/1.11

(58) Field of Classification Search .............. 606/1, 108; 623/1.11, 1.12, 1.23
See application file for complete search history.

(56) References Cited

U.S. PATENT DOCUMENTS

| | | | |
|---|---|---|---|
| 5,707,376 A | | 1/1998 | Kavteladze et al. |
| 5,968,052 A | * | 10/1999 | Sullivan et al. ............... 623/1.11 |
| 7,052,511 B2 | | 5/2006 | Weldon et al. |
| 2004/0006380 A1 | | 1/2004 | Buck et al. |
| 2005/0021123 A1 | | 1/2005 | Dorn et al. |
| 2005/0060016 A1 | | 3/2005 | Wu et al. |
| 2005/0080476 A1 | * | 4/2005 | Gunderson et al. .......... 623/1.11 |
| 2007/0060999 A1 | | 3/2007 | Randall et al. |

FOREIGN PATENT DOCUMENTS

DE 29717110 11/1997

OTHER PUBLICATIONS

PCT/US2008088191, Aug. 28, 2009, William Cook Europe ApS Int'l Search Report.
PCT/US2008088191, Aug. 28, 2009, William Cook Europe ApS Written Opinion.

* cited by examiner

*Primary Examiner* — Ryan Severson
(74) *Attorney, Agent, or Firm* — Richard J. Godlewski

(57) ABSTRACT

A deployment handle (112) for an implant deployment device (10) facilitates withdrawal of a sheath (18). The deployment handle (112) includes two separate actuators: a trigger (130) and a sliding actuator (330). The trigger (130) can be used to effect small step-wise movement of a carriage (120) that is connected to a sheath (18) to be withdrawn. The sliding actuator (330) can be used to effect continuous movement of a carriage (120) to withdraw a sheath (18). In order to transmit movement of either the trigger (130) or the sliding actuator (330) to the carriage (120), a flexible rack (380) is used. The flexible rack (380) includes upper teeth (390) and lower teeth (395) for engagement with the trigger (130) and the sliding actuator (330) respectively. The ability of the flexible rack (380) to bend back on itself means that unnecessary elongation of the deployment handle (112) is avoided.

14 Claims, 7 Drawing Sheets

DEPLOYMENT HANDLE FOR AN IMPLANT DEPLOYMENT DEVICE

CROSS-REFERENCE TO RELATED APPLICATIONS

This application claims priority of provisional application Ser. No. 61/009,139, filed Dec. 26, 2007.

TECHNICAL FIELD

The present invention relates to a deployment handle for an implant deployment device, and to an implant deployment assembly.

BACKGROUND OF THE INVENTION

The use of delivery devices employing catheters has long been known for a variety of medical procedures, including procedures for establishing, re-establishing or maintaining passages, cavities or lumens in vessels, organs or ducts in human and veterinary patients, occlusion of such vessels, delivering medical treatments, and other interventions. For these procedures, it has also long been known to deliver an implant by means of a catheter, often intraluminally. For example, a stent, stent-graft, filter or occlusion device may be delivered intraluminally from the femoral artery for deployment.

For procedures in which a prosthesis or other device is implanted into a patient, the device to be implanted is normally held onto the catheter in a compressed state and then released from the catheter so as to expand to its normal operating state, prior to withdrawal of the catheter from the patient to leave the implant in position.

A variety of delivery mechanisms is known in the art. These generally involve positioning the implant on a distal part of a delivery device, that is, at an end furthest from the external manipulation end used by the clinician during the deployment procedure. The prosthesis or implant is normally held at the distal end of the catheter by a suitable restraining mechanism, restraining wires being just one known example. It is also conventional to cover the implant with a sheath in order to protect the implant and also the patient's vasculature or organs during the delivery process. Once the implant has been positioned at the location in which it is to be released, the sheath is retracted along the catheter to expose the implant. The implant is then expanded, either automatically, if the implant is of the self-expanding type, or by a suitable expanding mechanism if not, such as by means of an expansion balloon.

In cases where a sheath or other covering is provided, some delivery devices include a mechanism by which the sheath can be withdrawn by being pulled back towards the external manipulation end of the delivery device, that is, towards the surgeon or other clinician. The force required to withdraw such a sheath may be very large. Furthermore, the resistance to withdrawal of a sheath may vary, which can cause problems for a controlled and safe release of an implant.

The sheath may be withdrawn by the surgeon or clinician gripping the proximal end of the sheath with one hand, and the catheter with the other hand, and pulling back the sheath relative to the catheter. This method is not only hard work, but also the surgeon or clinician is unable to exert much control over the withdrawal process. Moreover, use of such force to withdraw a sheath may result in shifting of the previously carefully placed implant.

Known implant delivery handles are disclosed in U.S. Pat. No. 5,707,376, US 2007/0060999, US 2005/0060016 and U.S. Pat. No. 7,052,511.

SUMMARY OF THE INVENTION

The present invention seeks to provide an improved deployment handle for an implant deployment device and an improved implant deployment assembly.

According to a first aspect of the present invention there is provided an implant deployment device handle, including: at least one actuator including a coupling element to couple the actuator to a component of an implant deployment device to be withdrawn, wherein the coupling element includes a flexible rack; wherein the flexible rack is arranged to translate movement of at least one actuator in a withdrawal direction to corresponding withdrawal of a component coupled thereto.

The use of a flexible rack assists in reducing the size of the handle as the rack may be bent double within the handle.

The flexible rack preferably includes asymmetric teeth. These preferably include an abutment service and a sloping surface. Such asymmetric teeth allow incremental movements of the flexible rack in one direction only.

The flexible rack is preferably formed substantially as a "U" shape. This arrangement allows the components of the handle to be located in as small a volume as possible.

The flexible rack preferably includes a first set of teeth on a first surface and a second set of teeth on a second surface opposite the first surface. This arrangement assists in the minimizing the size of the handle.

According to a second aspect of the present invention, there is provided an implant deployment device handle, including: a first actuator and a second actuator; at least one coupling element to couple the first actuator and the second actuator to a component of an implant deployment device to be withdrawn; the first actuator operable to withdraw a component of an implant deployment device coupled thereto by a first distance by a single actuation thereof; the second actuator operable to withdraw a component of an implant deployment device coupled thereto by a second distance by a single actuation thereof; wherein the second distance is greater than the first distance, and wherein the first actuator is operable to be actuated a plurality of times in order to withdraw the component by the second distance.

The inclusion of two actuators enables the user to select whether controlled step-wise actuation or a continuous withdrawal is used.

The coupling element is preferably connected to a withdrawal member, the withdrawal member including a connector for a component to be withdrawn. Preferably, the coupling element translates movement of an actuator to the withdrawal member thereby to effect withdrawal of a component. This provides a convenient way of causing withdrawal of the component to be withdrawn by means of the first actuator and/or the second actuator.

The coupling element preferably couples both the first actuator and the second actuator to a component to be withdrawn. Use of only a single coupling element to couple two actuators to a component to be withdrawn reduces the number of components required within the handle.

The first actuator is preferably able to move between a proximal position and a distal position, and wherein movement towards the proximal position is in a withdrawal direction, and wherein the first actuator is biased into its distal position. With this arrangement, the user only needs to impart effort when withdrawal is desired; this facilitates the use of the handle and withdrawal of the component. The first actuator may be a trigger.

The second actuator is preferably a sliding actuator able to slide from a distal position to a proximal position, and wherein movement from the distal position to the proximal position is in a withdrawal direction. A sliding actuator allows withdrawal of the component in a single continuous movement, or in a series of smaller manually controlled proximal movements.

Preferably the coupling element includes a flexible rack. The flexible rack may include a first set of teeth on a first surface and a second set of teeth on a second surface opposite the first surface. In the preferred embodiment, the first actuator engages with at least one of the first set of teeth and the second actuator engages with at least one of the second set of teeth. This arrangement allows for a compact design.

According to a third aspect of the present invention, there is provided an implant deployment device handle, including: a trigger operable to withdraw a component of an implant deployment device coupled thereto by a first distance by a single actuation thereof; a slidable actuator operable to withdraw a component of an implant deployment device coupled thereto by a second distance by a single actuation thereof; wherein the second distance is greater than the first distance, and wherein the first actuator is operable to be actuated a plurality of times in order to withdraw the component by the second distance; and wherein a flexible rack is arranged to translate movement of the trigger and of the slidable actuator in a withdrawal direction to corresponding withdrawal of a component coupled thereto.

According to a fourth aspect of the present invention there is provided a kit including an implant deployment device including a component to be withdrawn, and a deployment handle as described above.

The component to be withdrawn may be a sheath for covering an implant to be deployed.

The kit may include an implant to be deployed. The implant may be a stent, a stent graft, a filter or an occlusion device.

BRIEF DESCRIPTION OF THE DRAWING

Embodiments of the present invention are described below, by way of example only, with reference to the accompanying drawings, in which.

DETAILED DESCRIPTION

It is to be understood that the Figures are schematic and do not show the various components in their actual scale. In many instances, the Figures show scaled up components to assist the reader.

In this description, when referring to a deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

On the other hand, when referring to an implant such as a stent or stent graft, the term proximal refers to a location that in use is closest to the patient's heart, in the case of a vascular implant, and the term distal refers to a location furthest from the patient's heart.

Figure 1:
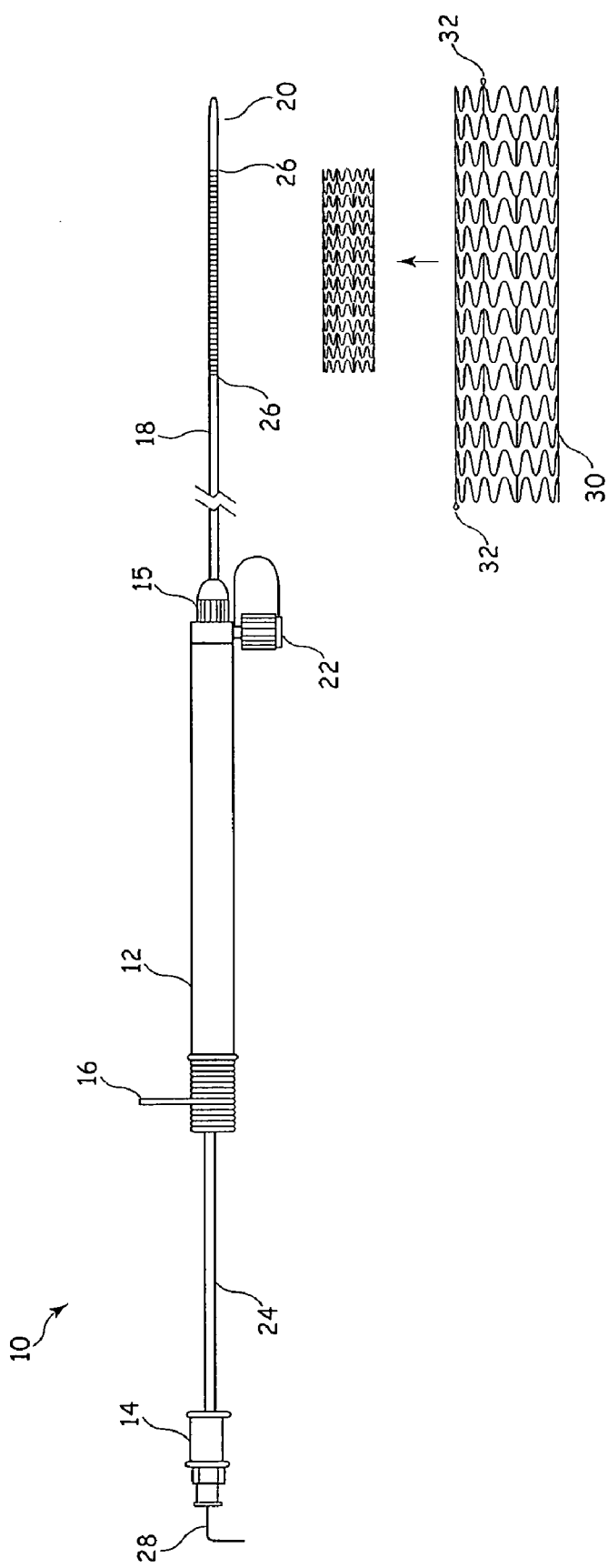
FIG. 1 is a side elevational view of an example of a known stent delivery device which can be used with a deployment handle according to the teachings herein.
Figure 2:
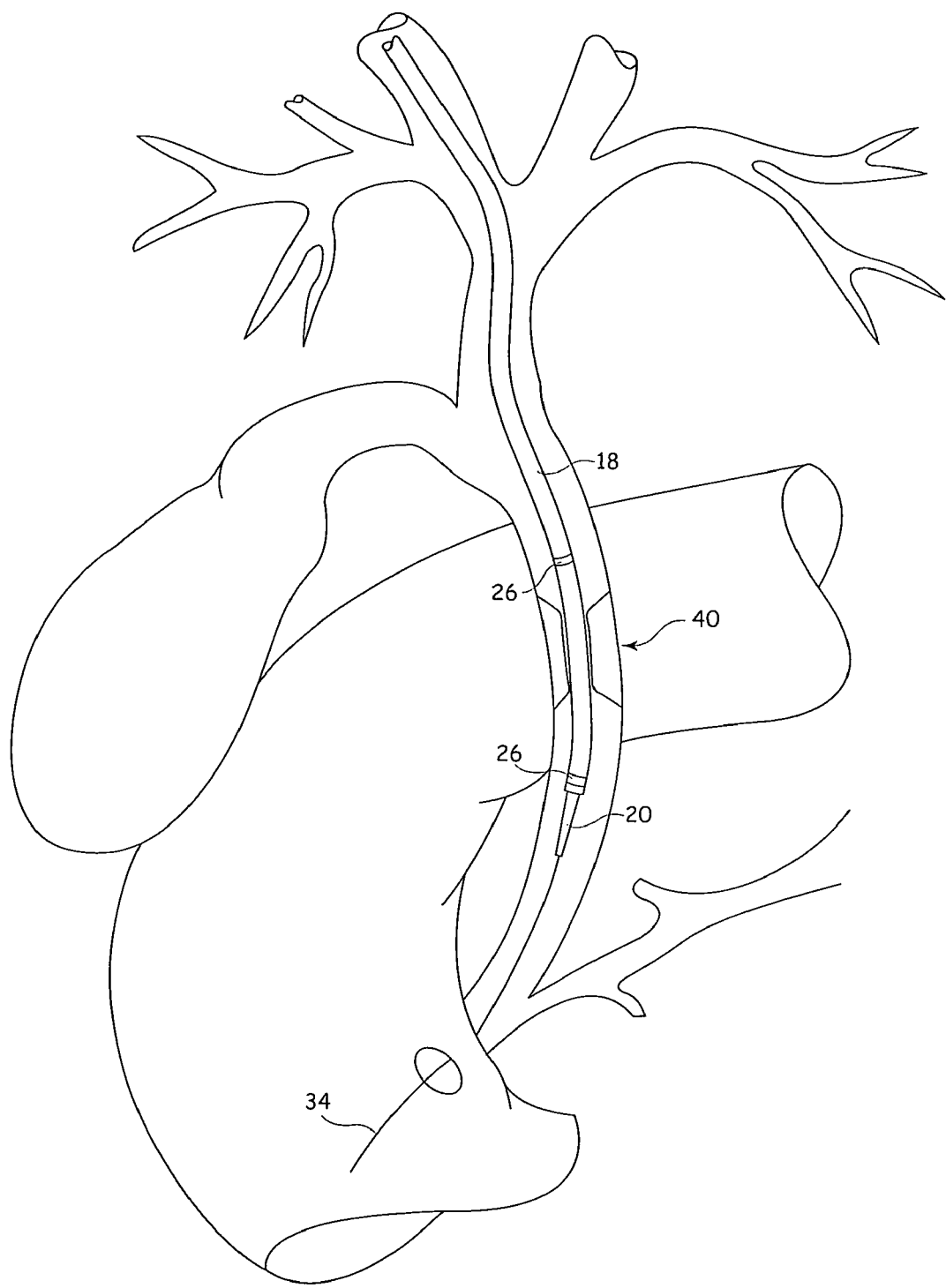
FIGS. 2 and 3 show the stent delivery device of FIG. 1 during deployment of a stent.
Figure 3:
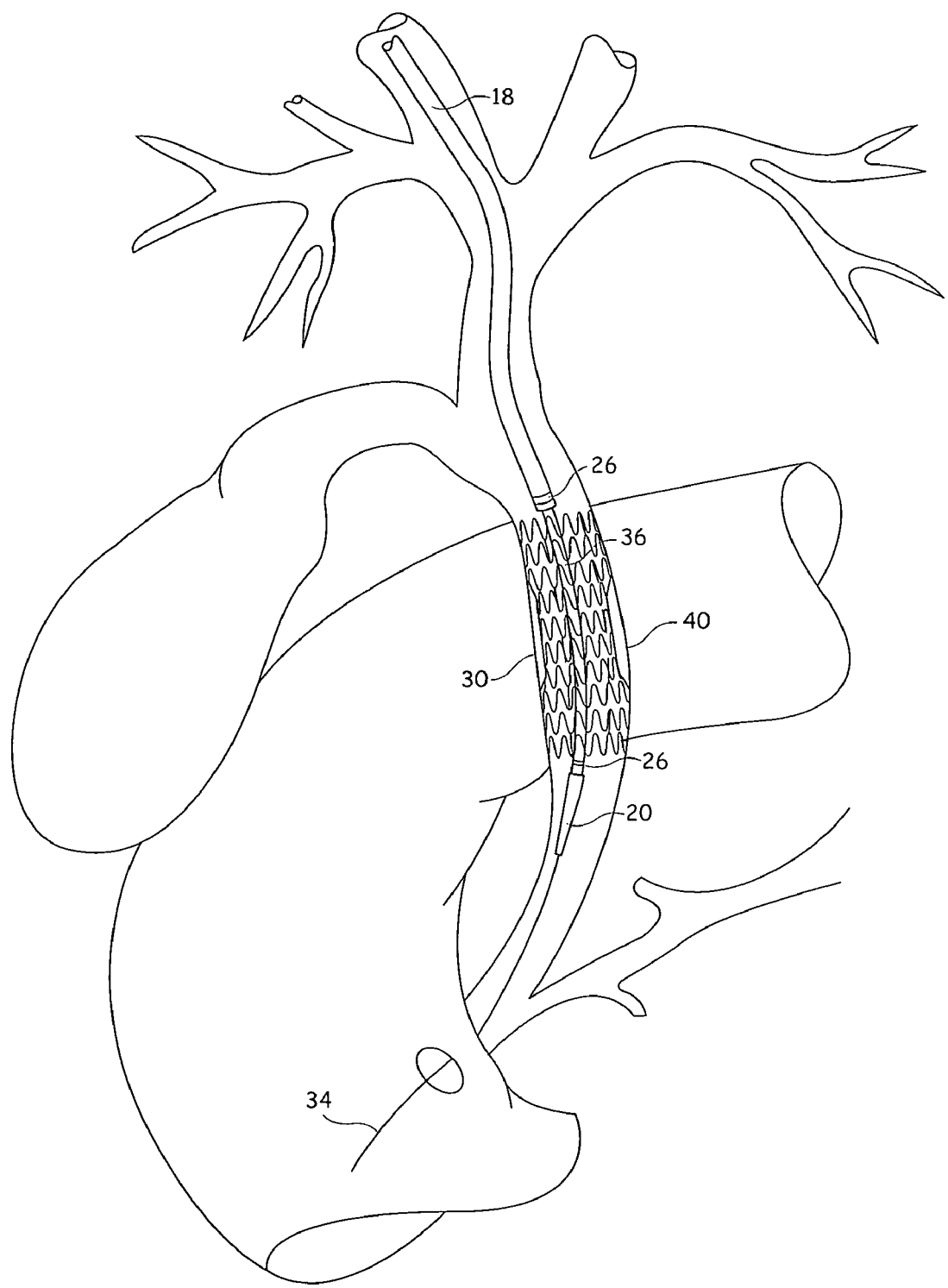

The example of delivery system shown in FIGS. 1 to 3 is the applicant's delivery system for its Zilver™ stent and in particular for its Zilver™ biliary stent.

The delivery assembly 10 shown in FIG. 1 includes a tubular handle 12, conventionally made of a plastics material, and a hub 14, also made of a plastics material. A safety lock 16 is removably fitted into a portion of the handle 12, for purposes to be described below.

An introducer catheter (or sheath) 18, made of any of the conventional or otherwise suitable catheter materials known in the art, extends from and is attached to the handle 12, in this example by a threaded nut 15. Housed within the introducer catheter 18 is an inner catheter 36 (visible in FIG. 3) which carries stent 30 and which is provided at its distal end with a flexible introducer tip 20. The inner catheter 36 has a bore passing therethrough for the introduction of a guide wire 34, shown in FIGS. 2 and 3.

The handle 12 is provided with a side arm flushing port 22, of conventional form, for flushing the space inside the introducer catheter 18.

The hub 14 is fixed to a metal cannula 24 which is itself attached to the inner catheter 36.

The delivery assembly 10 is provided with radiopaque markers 26. In this example, the proximal marker 26 is located on the introducer catheter 18, while the distal marker 26 is provided on the inner catheter 36, as will be apparent from FIG. 3.

The hub 14 is provided with an inner support stylet 28 operable to receive and support a guide wire 34, which guide wire 34 passes through the inner stylet 28, the hub 14, the metal cannula 24, the inner catheter 26 and out of distal end of the introducer tip 20.

The distal end of the inner catheter 36, adjacent the introducer tip 20, supports a stent 30, in this example a Zilver™ biliary stent obtainable from the applicant. The introducer catheter 18 overlies and acts as a holding sheath for the stent 30. This stent 30 is provided, in this example, with its own radiopaque markers 32, in a form known in the art.

The safety lock 16 acts to lock the metal cannula 24 in an extended position relative to the handle 12, as shown in FIG. 1, and thus to lock the introducer catheter 18 over the inner catheter 36, until the time of deployment.

Referring now to FIGS. 2 and 3, a stent is deployed, in this case in a biliary tract of a patient, by first introducing a guide wire 34 through an access catheter (not shown) across the distal segment of the target lesion 40 of the biliary tract. Once the guide wire 34 is in place, the introducer catheter 18 is fed over the guide wire 34 until the distal end of the introducer catheter 18 is over the target lesion 40. During this process the introducer catheter 18 is flushed with saline solution through the side arm flushing port 22.

Once the introducer catheter 18 has been located at the deployment site, the stent 30 held by the delivery assembly 10 is ready to be deployed. This position of the delivery assembly 10 is shown in FIG. 2, with the two markers 26 appearing either side of the target lesion site 40.

In order to deploy the stent 30, the safety lock 16 is removed, which allows the handle 12 to be slid over the metal cannula 24. In other words, once the safety lock 16 has been removed, the handle 12 can be pulled back whilst holding the hub 14 steady. This action of pulling back the handle 12 retracts the introducer catheter 18 from the inner catheter 36 with the result that the stent 30 is exposed and allowed to expand gradually as the introducer catheter 18 moves backwards relative to the inner catheter 36. FIG. 3 shows the introducer catheter 18 fully withdrawn and the stent 30 fully deployed at the target lesion 40.

Once the stent 30 has been deployed, the delivery assembly can be withdrawn by pulling the handle 12 and the hub 14 together in a withdrawal direction, that is, out of the patient. This procedure is known in the art in particular in connection with deployment of the applicant's Zilver™ stent.

Figure 4:
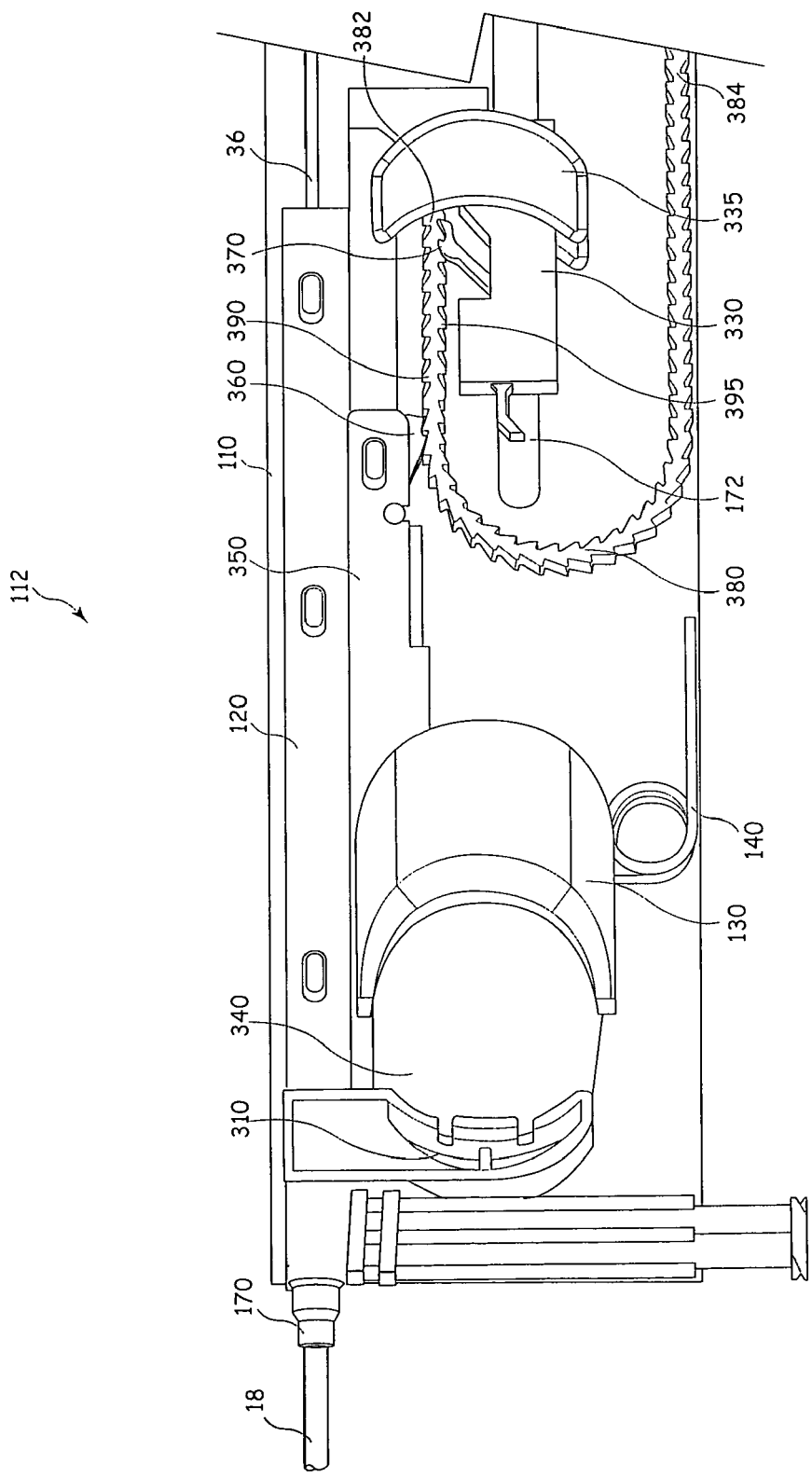
FIG. 4 shows in perspective the arrangement of a preferred deployment handle.
Figure 5:
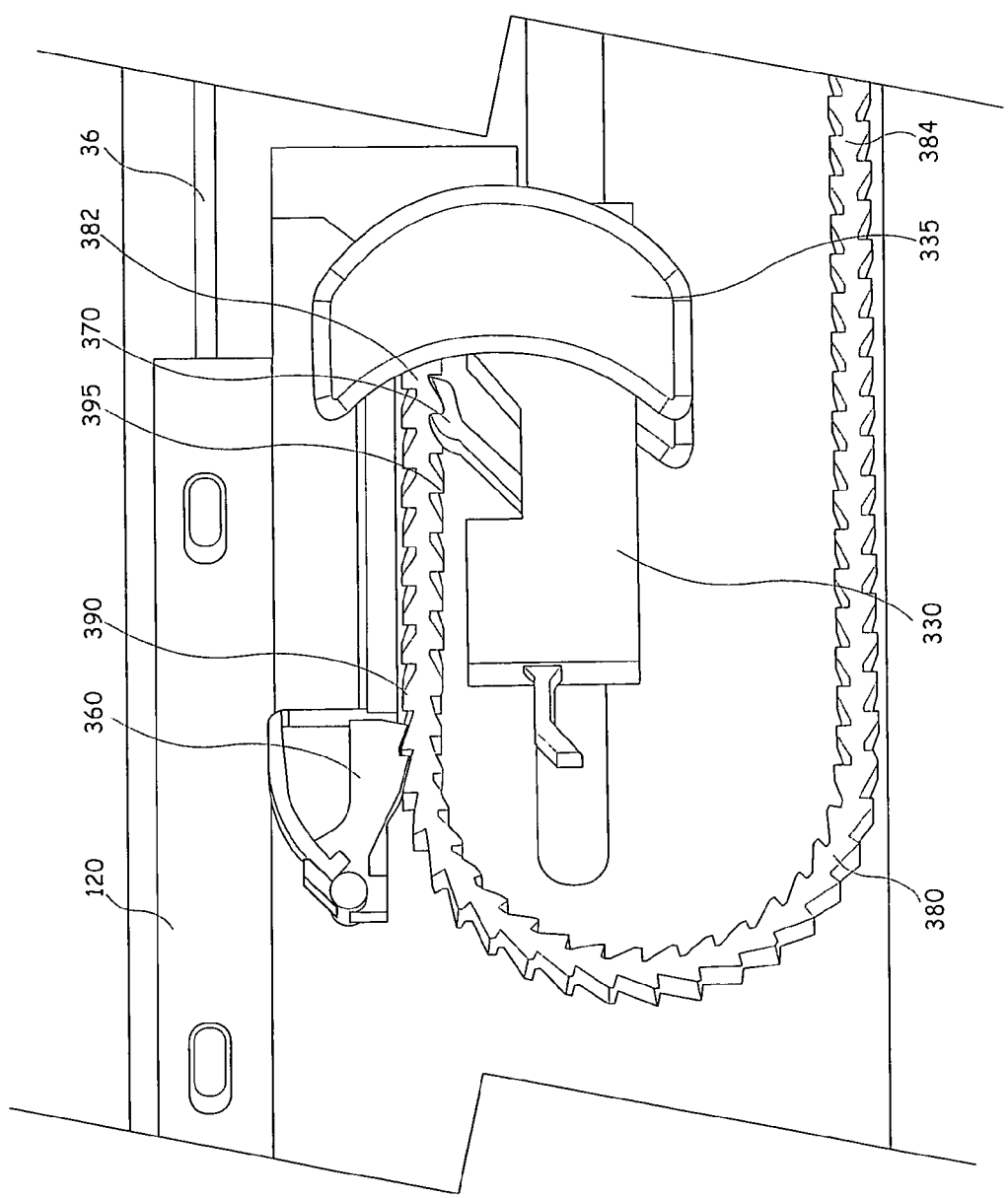
FIG. 5 shows an enlargement of part of FIG. 4.

Referring now in particular to FIGS. 4 and 5, the components found within a preferred embodiment of a deployment handle 112 are now described.

The deployment handle 112 includes a deployment handle body 110, which is formed of two parts, a "lower" part and an "upper" part (not shown). Together these form an outer casing for the working components of the deployment handle 112 having an overall size and shape suited to be hand-held.

The inner catheter 36 runs longitudinally through the deployment handle 112, which is located at the proximal end thereof. The deployment handle 112 includes a carriage 120 that is connected to the sheath 18 via a connection element 170. The carriage 120 is able to slide in a proximal direction (towards the right as shown in FIGS. 4 and 5) and co-operates with two actuators: a trigger 130 and a sliding actuator 330.

The trigger 130 is able to move back and forth (proximally and distally) by approximately 5 mm. It is located such that in its distal position it overlaps a finger hole 340 positioned towards the distal end of the casing 110 so that it can be actuated by a finger of a user. In its proximal position, the trigger 130 is aligned with the proximal edge of the finger hole 340, further proximal movement of the trigger 130 thereby being prevented. The trigger 130 is biased into its distal position by a coiled torsion spring 140 that abuts the trigger 130 and the edge of the casing 110. The trigger 130 includes a proximally extending trigger extension 350 that includes, at the proximal end thereof, trigger extension teeth 360. The function of these is described below.

Figure 6:
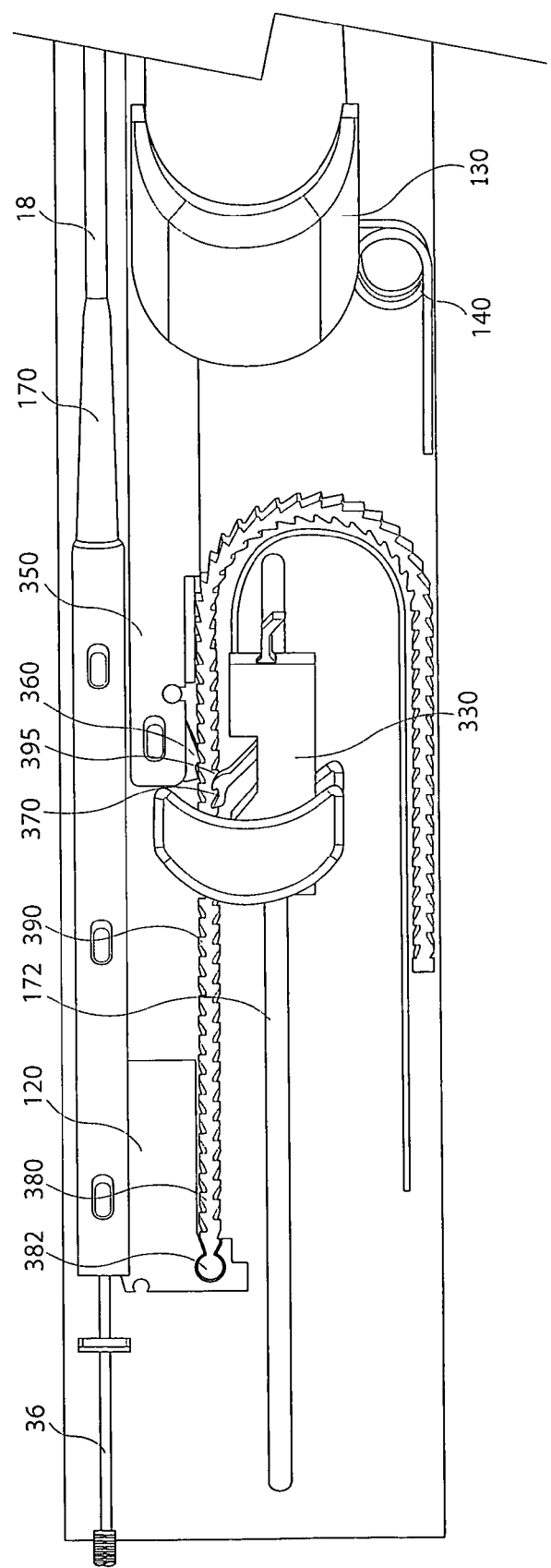
FIGS. 6 and 7 show schematic diagrams of a deployment handle in use.
Figure 7:
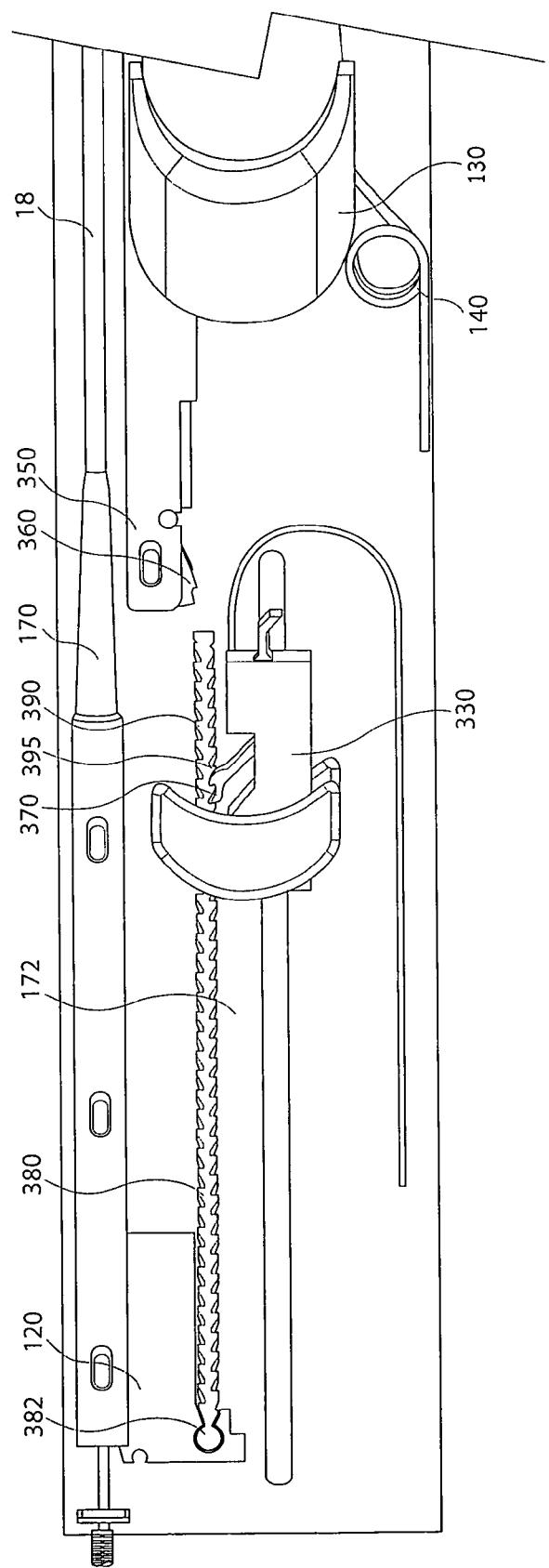

The sliding actuator 330 is able to slide proximally and distally along the handle within a guide channel 172 (see FIGS. 6 and 7). The sliding actuator 330 includes a knob 335 that extends through a longitudinal slot in the casing 110 of the deployment handle 112 so that it can be accessed by a user. The sliding actuator 330 includes a hook 370, the function of which is described below.

The trigger extension teeth 360 and the sliding actuator hook 370 are able to engage with upper teeth 390 and lower teeth 395 respectively of a moveable double-sided flexible rack 380. The flexible rack 380 may be made from nylon or polyethylene for example. The flexible rack 380 is fixed at one end to the carriage 120 such that movement of the flexible rack 380 causes corresponding movement of the carriage 120. The flexible rack 380 has a leading end 382 (the end attached to the carriage 120) and a trailing end 384. The flexible rack 380 forms a U-shape within the deployment handle 112 wherein its leading end 382 is located above its trailing end 384, and the curved part of the "U" is towards the distal end of the handle.

The teeth 390, 395 of the flexible rack 380 are asymmetric such that they include an abutment surface and a sloping surface. The trigger extension teeth 360 and the sliding actuator hook 370 have a shape that corresponds to the teeth 390, 395. The trigger extension teeth 360 and the sliding actuator hook 370 thus engage with the teeth 390, 395 such that movement of the trigger 130 or the sliding actuator 330 in a proximal direction causes the leading end 382 of the flexible rack 380 to move proximally because the abutment surfaces of the teeth 390, 395 are engaged with the trigger extension teeth 360 or the sliding actuator hook 370. However, when movement of the trigger 130 or the sliding actuator 330 is in a distal direction, the trigger extension teeth 360 and the sliding actuator hook 370 are able to slide over the sloping surfaces of the teeth 390, 395 due to resiliency of the trigger extension 350 and the sliding actuator hook 370. This enables the flexible rack 380 to remain longitudinally stationary as the trigger 130 or the sliding actuator 330 moves in the distal direction.

A lock button 310 that extends through an aperture in the casing 110 of the deployment handle 112 is able to engage the carriage 120 to prevent movement thereof.

FIGS. 6 and 7 illustrate the arrangement of the components after partial withdrawal of a sheath 18 (FIG. 6) and full withdrawal (FIG. 7). It can be seen that the trigger 130 when moved in a proximal direction by a finger of the user, causes proximal movement of the trigger extension 350 and the trigger extension teeth 360. Engagement of the trigger extension teeth 360 against the abutment surface of the upper teeth 390 of the flexible rack 380 causes proximal movement of the leading end 382 of the flexible rack 380. As the flexible rack 380 is attached to the carriage 120, which in turn is attached to the sheath 18 via the connection element 170, movement of the trigger 130 in a proximal direction by approximately 5 mm causes movement of the carriage 120 in a proximal direction to the same extent, and thus withdrawal of the sheath 18 to the same extent. Release of the trigger 130 results in it returning to its distal position by means of the coiled torsion spring 140. The trigger extension teeth 360 are able to slide over the sloping surfaces of the upper teeth 390 and reengage with upper teeth 390 further behind the leading edge 382 of the flexible rack 380. It can thus be seen that repeated actuation and release of the trigger 130 results in controlled, stepwise movement of the flexible toothed rack 380, the carriage 120 and thus withdrawal of the sheath 18 in a proximal direction.

The carriage 120 may also be moved in a single action in a proximal direction by means of the sliding actuator 330. As indicated above, the sliding actuator 330 is able to slide proximally and distally along a guide channel 172. The sliding actuator hook 370 engages with the abutment surface of the lower teeth 395. Proximal movement of the sliding actuator 330 thus causes movement of the leading edge 382 of the flexible rack 380 in the proximal direction. The sloping edges of the lower teeth 395 and the sliding actuator hook 370 are able to slide over one another when the flexible rack 380 is being pushed by the trigger extension teeth 360 due to the resiliency of the sliding actuator hook 370. The sliding actuator 330 is able to move along the length of the guide channel 172 and thus cause the flexible rack 380 and the carriage 120 to move by the same extent and for the sheath 18 to be withdrawn by the same extent.

It can thus been seen, that this arrangement allows for either withdrawal of the sheath 18 in small steps (using trigger 130) and/or in a continuous movement (using sliding actuator 330).

In use, the surgeon or clinician threads the deployment handle 112 over the inner catheter 36 and connects the sheath 18 to be withdrawn to the connection element 170. The lock is disengaged from the carriage 120 by depressing the lock button 310. This allows movement of the carriage 120. The surgeon can then select which mode of operation to use at any one time. For example, at one stage of deployment, they may wish to ensure that sheath withdrawal only occurs in very slow, controlled steps. At this stage, the trigger 130 can be used to effect withdrawal. At other times, or in other situations, the surgeon may wish to have more of a feel of the process of uncovering an implant as it occurs. For this reason, they may prefer to use the sliding actuator 330. For example, when using the sliding actuator 330, it may be possible to feel (for example, through unanticipated resistance) whether there are any problems with the withdrawal process.

It can be seen, therefore, that according to the user's preference, one stage of withdrawal could be effected using the trigger actuator 130 and a different stage (which could be earlier or later) the sliding actuator 330 could be used. In some embodiments, it may not be possible to use the trigger actuator 130 after the sliding actuator 330 if the sliding actuator has been moved in a proximal direction to its full extent.

The above-described deployment handle provides the choice to the user of whether, at a particular stage of the withdrawal process, the sheath 18 is withdrawn in several small steps using the trigger 130, or in a single continuous movement using the sliding actuator 330. The sliding actuator 330 may even be used to effect withdrawal in several manually-controlled steps rather than in a single step.

An advantage of inclusion of the trigger 130 is that the handle can be operated single-handedly by the user when the trigger 130 is used to effect withdrawal.

The use of a flexible rack 380 provides several advantages. By its formation into a "U" shape a relatively long range of movement can be obtained whilst keeping the handle a convenient size. The flexibility also allows the sloping surfaces of the trigger extension teeth 360 and the sliding actuator hook 370 to pass over the sloping surfaces of the rack teeth 390, 395 as the trigger 130 or the sliding actuator 330 moves in a distal direction.

The skilled person will appreciate that the described deployment handle 112 could be used to move or withdraw other components of an implant deployment device 10. For example, it could be used to withdraw restraining wires that hold an implant in a constrained configuration.

Another advantage of the disclosed handle is that it can be used as part of a rapid exchange system, in particular in connection with removal of the sheath in a single action by means of the sliding actuator 330.

Other uses of the disclosed deployment handle 112 will be envisaged by the skilled person.

The disclosures of U.S. 61/009,139 from which the present application claims priority, and in the Abstract, are incorporated herein by reference.

What is claimed is:

1. An implant deployment device handle, including:
a first actuator and a second actuator;
a coupling element to couple the first actuator and the second actuator to a component of an implant deployment device to be withdrawn, wherein the coupling element includes a double-sided flexible rack, the flexible rack including a first surface and a second surface opposite the first surface and a first set of teeth on the first surface and a second set of teeth on the second surface;
wherein the flexible rack is arranged to translate movement of the at least one actuator in a withdrawal direction to corresponding withdrawal of a component coupled thereto;
wherein the first actuator is operable to withdraw a component of an implant deployment device coupled thereto by a first distance by a single actuation thereof;
wherein the second actuator is operable to withdraw a component of an implant deployment device coupled thereto by a second distance by a single actuation thereof;
wherein the second distance is greater than the first distance, and wherein the first actuator is operable to be actuated a plurality of times in order to withdraw the component by the second distance.

2. The handle of claim 1, wherein the teeth are asymmetric.

3. The handle of claim 2, wherein the teeth include an abutment surface and a sloping surface.

4. The handle of claim 1, wherein the flexible rack is formed substantially as a "U" shape.

5. The handle of claim 1, wherein flexible rack is connected to a withdrawal member, the withdrawal member including a connector for a component to be withdrawn, and wherein the flexible rack translates movement of an actuator to the withdrawal member thereby to effect withdrawal of a component.

6. The handle of claim 1, wherein the first actuator is able to move between a proximal position and a distal position, wherein movement towards the proximal position is in a withdrawal direction, and wherein the first actuator is biased into its distal position.

7. The handle of claim 6, wherein the first actuator is a trigger.

8. The handle of claim 1, wherein the second actuator is a sliding actuator able to slide from a distal position to a proximal position, and wherein movement from the distal position to a proximal position is in a withdrawal direction.

9. The handle of claim 1, wherein the first actuator engages with at least one of the first set of teeth and the second actuator engages with at least one of the second set of teeth.

10. An implant deployment device handle, including:
a trigger operable to withdraw a component of an implant deployment device coupled thereto by a first distance by a single actuation thereof;
a slidable actuator operable to withdraw a component of an implant deployment device coupled thereto by a second distance by a single actuation thereof;
wherein the second distance is greater than the first distance, and wherein the first actuator is operable to be actuated a plurality of times in order to withdraw the component by the second distance; and
wherein a double-sided flexible rack is arranged to translate movement of the trigger and of the slidable actuator in a withdrawal direction to corresponding withdrawal of a component coupled thereto;
wherein the flexible rack includes a first surface and a second surface opposite the first surface, and a first set of teeth on the first surface and a second set of teeth on the second surface.

11. A kit including an implant deployment device including a component to be withdrawn and the handle of claim 1 or 10.

12. The kit of claim 11, wherein the component to be withdrawn is a sheath for covering an implant to be deployed.

13. The kit of claim 11, wherein the kit includes an implant to be deployed.

14. The kit of claim 13, wherein the implant is a stent, a stent graft, a filter or an occlusion device.

* * * * *